US00PP13717P39

(12) United States Plant Patent
Beckmann

(10) Patent No.: US PP13,717 P3
(45) Date of Patent: Apr. 8, 2003

(54) POINSETTIA PLANT NAMED 'FISSON BECKPINK'

(75) Inventor: Karl-Rudolf Beckmann, Goennebek (DE)

(73) Assignee: Florfis AG, Binningen (SE)

( * ) Notice: Subject to any disclaimer, the term of this patent is extended or adjusted under 35 U.S.C. 154(b) by 0 days.

(21) Appl. No.: 09/866,690

(22) Filed: May 30, 2001

(65) Prior Publication Data

US 2002/0184688 P1 Dec. 5, 2002

(51) Int. Cl.[7] ..... A01H 5/00

(52) U.S. Cl. ..... Plt./306

(58) Field of Search ..... Plt./306, 307

*Primary Examiner*—Bruce R. Campell
*Assistant Examiner*—Michelle Kizilkaya
(74) *Attorney, Agent, or Firm*—Foley & Lardner

(57) ABSTRACT

A new and distinct cultivar of Poinsettia plant named 'Fisson Beckpink', as described and illustrated, and particularly characterized by the combined features of intense hot pink bract color; medium sized, star-shaped inflorescence with distinctly lobed bracts; uniform dark-green foliage, with relatively strong lobes; moderately compact, well-branched, and round plant habit; medium (mid season) flowering response; and good after-sale keeping quality of the bracts and the cyathia.

1 Drawing Sheet

LATIN NAME OF THE GENUS AND SPECIES OF THE PLANT CLAIMED

*Euphorbia pulcherrima*

VARIETY DENOMINATION

'Fisson Beckpink'

BACKGROUND OF THE INVENTION

The present invention relates to a new and distinct cultivar of Poinsettia plant known by the cultivar name 'Fisson Beckpink' and botanically known as *Euphorbia pulcherrima*.

'Fisson Beckpink' was derived from a naturally occurring mutation in the variety 'Fisson', (U.S. Plant Pat. No. 9,365). 'Fisson' is characterized by brilliant red bracts with pointed lobes, dark-green foliage and well-branched, round plant habit. The mutation was discovered by Karl-Rudolf Beckmann, the inventor, in his greenhouse in Gönnebek, Germany, among a group of flowering plants, in the fall of 1996.

A single, branched plant had completely mutated and displayed an intense pink bract color, instead of the red color of the parent variety. This plant was taken to Hillscheid, Germany, Germany, in winter 1996/97. In the spring of 1997, the plant was asexually multiplied by taking shoot tip cuttings in Hillscheid, Germany, by Katharina Zerr.

The resulting plants were examined in the autumn trial cultivation in 1997 and proved to be absolutely uniform. This was confirmed in the horticultural trial cultivation conducted on a larger scale both in Langley, Canada, and in Hillscheid, Germany, in the fall of 1998.

'Fisson Beckpink' has not been observed under all possible environmental conditions. The phenotype may vary significantly with variations in environment such as temperature, light intensity and day length.

BRIEF DESCRIPTION OF THE INVENTION

The following traits have been repeatedly observed and are determined to be basic characteristics of 'Fisson Beckpink', which in combination distinguish this Poinsettia as a new and distinct cultivar:

1. intense hot pink bract color;
2. medium sized, star-shaped inflorescence with distinctly lobed bracts;
3. uniform dark-green foliage, with relatively strong lobes;
4. moderately compact, well-branched, and round plant habit;
5. medium (mid season) flowering response; and
6. good after-sale keeping quality of the bracts and the cyathia.

Of the may commercial cultivars known to the inventor, the most similar in comparison to 'Fisson Beckpink' is the parent cultivar 'Fisson' and the related cultivar 'Fissonosa' (U.S. Plant Pat. No. 10,182).

In comparison to 'Fissonosa', 'Fisson Beckpink' has a different bract color, rose instead of red, weaker anthocyanin coloration of stems, petioles and leaf veins, and has bracts with a somewhat more wrinkled surface.

In comparison to 'Fissonosa', 'Fisson Beckpink' has a more intense and and more uniform bract color. There is hardly any difference of intensity of the color between the larger and the smaller bracts, in contrast to the inflorescence of 'Fissonosa'. Furthermore, the bracts of 'Fisson Beckpink' tend to becoming somewhat rugose or wrinkled with maturing, while those of 'Fissonosa' remain relatively smooth.

BRIEF DESCRIPTION OF THE DRAWING

The accompanying color photographic drawing shows typical inflorescence and foliage of 'Fisson Beckpink', with colors being as true as possible with illustrations of this type. The photograph shows a flowering potted plant. The age of the plant is 15 weeks from the planting of rooted cuttings.

DETAILED DESCRIPTION OF THE INVENTION

The plants described were grown in a greenhouse in Langley, British Columbia, Canada, in the fall of 1998. Rooted cuttings were planted into 15 cm pots on August 10, and were pinched 14 days later, leaving 8 nodes. The minimum temperature was 23° C. until October 10, 20° C. to mid-November, and lower thereafter. The plants initiated flowers under natural short-day conditions in the fall.

The following observations, measurements and comparisons describe plants grown in Langley, British Columbia, Canada, under greenhouse conditions which approximate those generally used in commercial practice.

Observations and measurements were mainly taken in early December, at the beginning of full flowering. In the following description color references are made to The Royal Horticultural Society Colour Chart (R.H.S.). The color values were determined indoors in a north light.

Classification:

*Botanical.*—*Euphorbia pulcherrima.*

*Commercial.*—Poinsettia cv. Fisson Beckpink.

Parentage: Naturally occurring mutation of 'Fisson'

Plant:

*Form.*—Shrub, self-branching.

*Growth habit.*—Relatively compact, free branching, pinched plants are bushy and round in shape.

*Height* (*without pot*).—32.0 cm.

*Width.*—51.7 cm.

*Average number of branches.*—9.9.

*Branch length.*—About 24–26 cm

*Internode length.*—20–25 mm

*Average number of inflorescences.*—8.1

*Average height of inflorescences.*—25–35 mm

*Stem color.*—Light green, RHS 143 A–B, weak infusion of anthocyanin (reddish hue) may occur in parts.

*Rooting.*—Medium, about 20 days.

*Blooming habit.*—Begin under natural short day conditions in fall: botanically (cyathia open): around December 1; commercially (bracts colored, saleable): in late November.

*Flowering response time.*—About 9 weeks.

*Flowering season.*—Up to about 4 weeks.

*Keeping quality* (*shelf life*).—Relatively good even under unfavorable conditions: about 28 days.

Foliage:

*Shape.*—Basal part roughly triangular, with acute base, acuminated tip, and usually with distinct, pointed lobes.

*Leaf arrangement.*—Alternate

*Margin.*—Entire, apart from the lobes.

*Texture.*—Upper surface: smooth, only weakly veined, vein color is greenish, about RHS 146 D or lighter, the basal part of the midrib may have same reddish coloring as the petiole. Lower surface: smooth, except for the slightly protruding midrib and finer side veins, which are arranged in a pinnate pattern, the color of the veins is very light green, RHS 145 C.

*Size.*—Leaf blade: 12.7 cm long, 10.0 cm wide on average.

*Petiole.*—6.2 cm long; diameter 3 mm.

*Leaf color.*—Uniform dark-green. Mature foliage color: Upper surface RHS 139 A, under surface RHS 137 B. New foliage color: Somewhat variable, upper surface: near RHS 143 A, under surface near RHS 137 D.

*Petiole.*—Color: Dull red, about RHS 53 B or lighter.

*Aspect of leaves.*—Most often the petioles are horizontally or slightly upward directed, while the leaf blades show slightly downward.

Disease resistance: No special observations made

Flowering description:

*Whole inflorescence.*—Medium sized, almost flat, with the mature bracts horizontally or slightly downward directed, while the young bracts initially show somewhat upward, diameter 21.5 cm on average.

Bracts:

*Number of bracts per inflorescence.*—8–11.

*Shape.*—The basal part is roughly triangular, with acute base, distinct lobes with pointed tips, and with acuminate tip; the smaller, younger bracts are ellipticslly shaped and usually without lobes.

*Bract size.*—11.0 cm cm long, 9.6 cm wide.

*Texture.*—Surface somewhat wrinkled (rugose).

*Veins.*—Arranged in a pinnate pattern, they are hardly visible at the upper surface, while they slightly protrude at the lower surface. The vein color on the upper side corresponds closely to the bract color, while it is lighter on the lower surface: pink, RHS 51 A–B.

*Color.*—Generally brilliant hot-pink to rose, relatively uniform; upper surface,between: RHS 52A and RHS 46 D; the margins of some of the lower bracts may appear slightly lighter: 52 A–B; lower surface, between RHS 52 A and 52 B.

*Petiole.*—10–15 mm long, reddish, about RHS 46 D.

*Cyme.*—About 20–22 mm wide, about 10 cyathia in a tight cluster.

*Cyathia.*—Diameter 4–5 mm, length 13–15 mm (including peduncle and stamen).

*Cyathium color.*—Mainly light green, RHS 143 C, top light red, RHS 46 D.

*Nectar cups.*—1 or 2 per cyathium , 4 mm wide, bright yellow, usually no anthocyanin (reddish) coloring at the margin.

Reproductive organs:

*Stamens.*—Quantity: about 15 in a bundle; color: bright red; moderate pollen production, yellow RHS 12 A.

*Anther.*—Length 4 mm, filiform shape.

*Pistils.*—Light red style and stigma, RHS 46 D, 6-lobed stigma.

*Ovaries.*—Medium green, RHS 137 D, typical shape, triangular, 3 ovules.

*Fertility.*—Seed set was not observed, but most probably fertile.

I claim:

1. A new and distinct cultivar of Poinsettia plant named 'Fisson Beckpink', as described and illustrated herein.

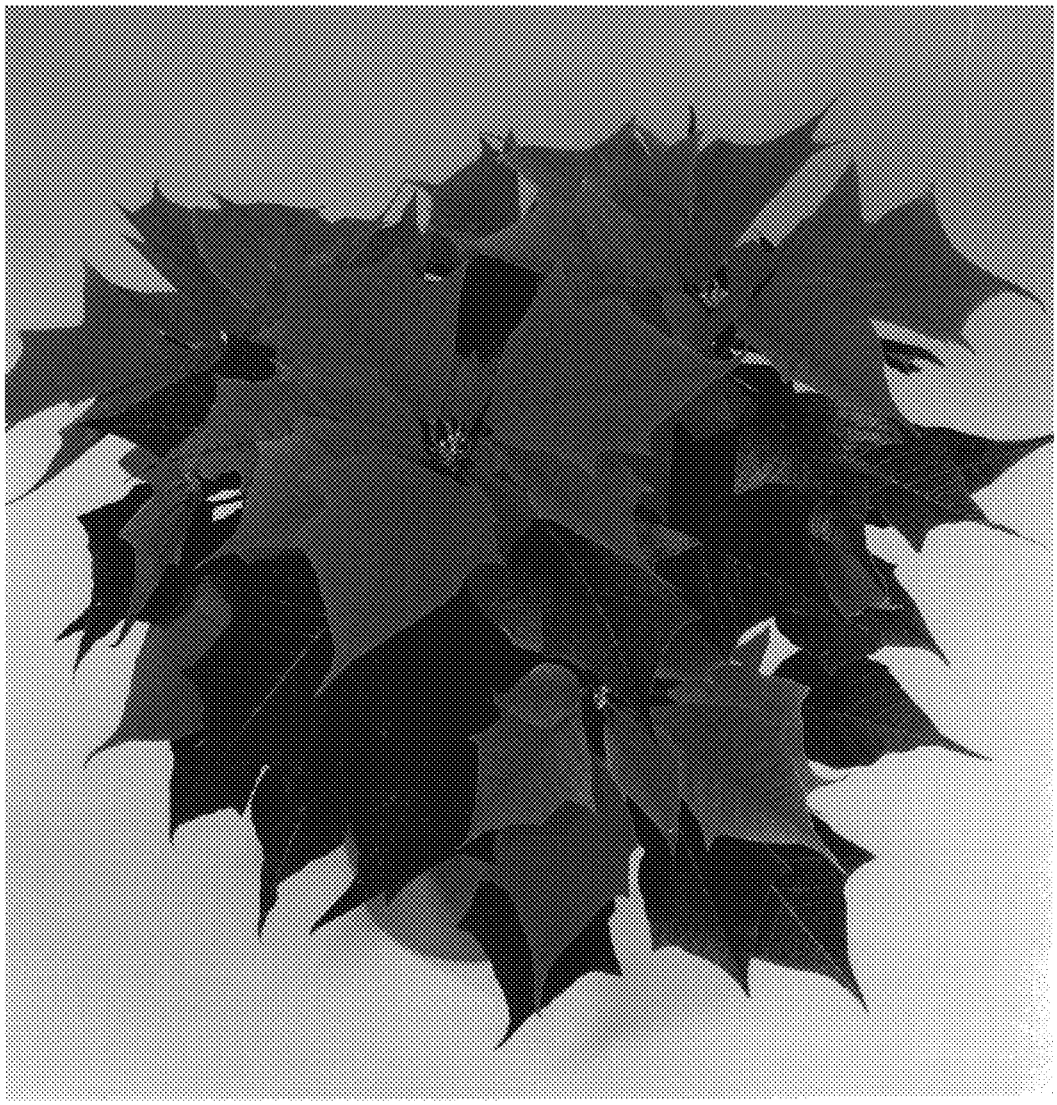

* * * * *